United States Patent [19]

Kramer

[11] 4,162,233

[45] Jul. 24, 1979

[54] ISOMERIZATION-ALKYLATION SYSTEMS COMPRISING A GR. III A LEWIS ACID AND A NON-REACTIVE APROTIC SOLVENT

[75] Inventor: George M. Kramer, Berkeley Heights, N.J.

[73] Assignee: Exxon Research & Engineering Co., Florham Park, N.J.

[21] Appl. No.: 889,033

[22] Filed: Mar. 22, 1978

[51] Int. Cl.² .................. B01J 31/02; B01J 27/10; C07C 3/18; C07C 5/24

[52] U.S. Cl. .................. 252/429 R; 585/942; 526/221; 526/281

[58] Field of Search ................. 252/429 R; 260/683.15 B, 683.76

[56] References Cited

U.S. PATENT DOCUMENTS

| | | | |
|---|---|---|---|
| 2,356,128 | 8/1944 | Thomas et al. | 260/79 |
| 2,515,138 | 7/1950 | Schutze et al. | 252/429 |
| 2,521,431 | 9/1950 | Walsh, Jr. et al. | 252/429 R |
| 2,678,957 | 5/1954 | Fontana et al. | 260/683.15 B |
| 2,965,693 | 12/1960 | Kramer | 260/683.53 |
| 3,725,500 | 4/1973 | Kramer | 260/683.75 |
| 4,048,095 | 9/1977 | Wojcik et al. | 252/429 R |
| 4,048,251 | 9/1977 | Cahn et al. | 260/683.75 |

FOREIGN PATENT DOCUMENTS

463727  3/1950  Canada ................. 252/429 R

*Primary Examiner*—P. E. Konopka
*Attorney, Agent, or Firm*—Albert P. Hailuin

[57] ABSTRACT

Novel acid systems are disclosed which are characterized as being capable of stabilizing high concentrations of tertiary cations, e.g., t-butyl cation, and further characterized as capable of forming carbonium ion salts containing both dimeric and monomeric anions. The ions undergo hydride and halide exchange with other alkanes and halides. The hydride transfer reaction renders them useful in isomerization and alkylation reactions.

19 Claims, No Drawings

ISOMERIZATION-ALKYLATION SYSTEMS COMPRISING A GR. III A LEWIS ACID AND A NON-REACTIVE APROTIC SOLVENT

BACKGROUND OF THE INVENTION

1. Field of the Invention

The present invention relates to novel acid systems that are capable of stabilizing high concentrations of tertiary cations and forming carbonium ion salts containing dimeric and monomeric anions. The ions undergo hydride and halide exchange with other alkanes and halides. The hydride transfer reaction renders them useful in isomerization and alkylation reactions.

2. Description of the Prior Art

Isomerization of a gasoline fraction to increase branching is one of the simplest of the common reactions of petroleum chemistry. Model studies have been carried out with butane, pentane and simple alicyclics that yield relatively uncomplicated product mixtures. For example, the butanes may be equilibrated fairly rapidly in contact with aluminum halides at temperatures of 100° C. or higher.

It is known that pure dry aluminum bromide is not an effective catalyst unless the system contains some trace of alkyl halide, alcohol, or a combination of an alkene and a proton source. Examples of aluminum bromide promoted isomerization catalyst systems are disclosed in U.S. Pat. Nos. 2,963,526; 2,987,563; 3,641,185; 3,758,623; and 3,946,088. Some of these patented catalyst systems include halogenated compounds, e.g., polyhalogenated benzenes and they are preferably promoted by promoters such as hydrogen halides, alkyl halides and water.

Another example of an isomerization catalyst is described in U.S. Pat. No. 3,725,500, the disclosure of which is incorporated herein by reference. In this patent, the catalyst comprises a mixture of aluminum halo bromide and a sulfur oxo halide, e.g., $AlBr_3/SO_2FCl$ mixtures. The catalyst composition is capable of stabilizing high concentrations of alkyl carbonium ions and it is useful in isomerization reactions.

The promoters in these catalyst systems lead to the formation of carbonium ions which initiate chain reactions leading to rearrangement of the hydrocarbon feedstock. A key step is the hydride transfer reaction involving hydrogen transfer from a hydrocarbon to a carbonium ion. Rearrangement of the new carbonium ion leads to isomerization.

The following equations illustrate these reactions:

Initiation:

Propagation:

(a) Hydrogen transfer - Bartlett-Condon-Schneider hydride transfer between n-butane and the tert.-butyl carbonium ion:

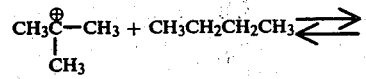

(b) Rearrangement of the sec.-butyl carbonium ion to the tert.-butyl carbonium ion:

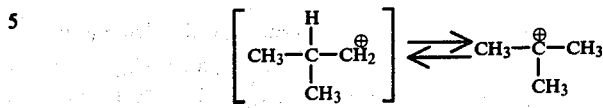

(C) Propagation step:

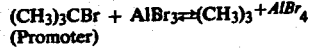

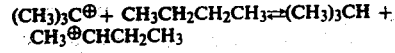

Conversion of n-butane into isobutane is of importance industrially, and is interesting as a prototype for catalytic isomerization of low-octane gasolines. Considerable amounts of n-butane are produced in cracking reactions and converted to isobutane, which is needed for synthesis of high octane blending components of motor gasoline by alkylation of olefins.

It is further known that high-octane gasoline can be obtained by catalytic recombination of $C_2$ to $C_5$ olefins and isoparaffinic hydrocarbons. The reactants in the alkylation process are generally contacted in the liquid phase at temperatures usually below about 100° F., although on occasion, higher temperatures may be utilized and at pressures varying from ambient to superatmospheric. The alkylation process is generally carried out in the presence of acidic catalyst such as sulfuric acid or liquid hydrogen fluoride as shown below:

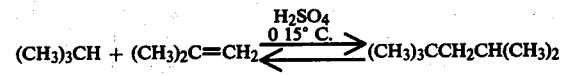

An example of an acid-catalyzed alkylation process is described mole U.S. Pat. No. 3,231,633.

The alkylation reaction has been regarded as proceeding through the acid catalyzed, addition of a t-butyl cation to butylene followed by a hydride transfer from isobutane. The latter reaction is favored in competition with the formation of higher isobutene polymers by use of excess alkane in the feedstock.

G. A. Olah et al. (J. Am. Chem. Soc., 85, 1328 (1963) and J. Am. Chem. Soc., 86, 1360 (1964) and D. M. Brouwer et al. (Proc. Chem. Soc., 147 (1964)) have reported that acid systems stronger than $H_2SO_4$ or HF have the ability to stabilize tertiary and in some cases secondary cations for a sufficient time to permit their observation by NMR spectroscopy. In principle this should permit the study of ionic equilibria engendered by the fast intermolecular hydride transfer reaction between the ions and alkanes that was studied under other conditions by Bartlett, Condon and Schneider (J. Am. Chem. Soc., 66, 1531 (1944)).

Typical acids that permit the detection of tertiary cations have been characterized in terms of the $H_o$ or Hammett acidity function. Suitable mixtures in $HSO_3F$ (i.e., $SbF_5 + HSO_3F$) have $H_o$'s greater than $-16$. Hammett acidity values for HF systems also have to be about this high. Typical HF systems involve one molar solutions of $TaF_5$, $NbF_5$ or $SbF_5$ in HF. The acidities of these solutions is much greater than HF itself ($H_o$ $= -11$), but these solutions are not generally useful for studying hydride transfer equlibria by NMR spectroscopy because all soluble alkanes are converted to carbonium ions.

DISCOVERY OF THE PRESENT INVENTION

It has now been discovered that solutions of strong Lewis acids having a "Selectively Parameter", $(I/E)_{MCP}$ greater than about 0.5 dissolved in a non-reactive aprotic solvent selected from the group consisting of halogenated $C_1$-$C_3$ alkanes, halogenated cyclopropane, and halogenated $C_2$-$C_3$ alkenes (wherein the $C_2$ and $C_3$ compounds have at least 2 halogen atoms) are capable of stabilizing high concentrations of ions, e.g., t-butyl carbonium ions, and also facilitate fast hydride transfer rections with other hydrocarbons such as isobutane and isopentane at low temperatures.

As indicated above, the strong Lewis acid to be used in accordance with the present invention, is defined in terms of its "Selectively Parameter" $(I/E)_{MCP}$. The term "Selectivity Parameter" has been previously defined and described (see G. M. Kramer, *J. Org. Chem.*, 40, 302 (1975) and G. M. Kramer, *J. Org. Chem.*, 40, 298 (1975), the disclosures of which are incorporated herein by reference). Thus, the "Selectivity Parameter" to be used for a given acid is obtained from 2 molar mixtures of the acid in a hydrogen halide containing the same anion.

The stabilized, strong acid systems of the present invention are useful in a plurality of hydrocarbon conversion processes, for example, the alkylations of olefins; the isomerization of hydrocarbon feedstocks; polymerization reactions; ect. and in "Paraffin Alkylation", i.e., the reaction of a high and low molecular weight paraffinic feed to yield paraffins of intermediate molecular weight. When the stabilized, strong acid systems of the invention are used in isobutane-propylene alkylation reactions, the acid systems are capable of producing 2,2- and 3,3-dimethylpentanes rather than the usual distribution of 2,3- and 2,4dimethylpentane obtained in sulfuric acid catalyzed alkylations. The mixture of 2,2- and 3,3-dimethylpentane has significant octane improvement over the more usual mixtures.

In the course of the discovery of the present invention it was found that direct measurement of the position of ionic equilbria in solution provides information on the importance of solvation in stabilizing the reacting pairs when compared with gas phase equilibra. The latter can be estimated from tabulations of ionic heats of formation, or measured directly by recently developed mass spectroscopic techniques. (For reference, see J. J. Solomon et al., *J. Am. Chem. Soc.*, 97, 2625 (1975) J. J. Solomon et al., *J. Am. Chem., Soc.*, 95, 4483 (1973); M. Meot-Ner et al., *J. Am. Chem. Soc.*, 98, 1025 (1976); J. J. Solomon et al., *J. Am. Chem. Soc.*, 98, 1567 (1976); J. J. Soomon et al., *J. Am. Chem. Soc.*, 96, 3727 (1974); and R. D. Wieting et al., *J. Am. Chem. Soc.*, 96, 7552 (1974)).

Unfortunately, equilibria of the following:

$$R_1{}^+ + R_2H \rightleftharpoons R_1H + R_2{}^+$$

are difficult to assess in many of the $SbF_5$ acid systems used to stabilize cations because these acids often oxidize all the alkanes to carbonium ions.

In principle, oxidation might be minimized by forming the carbonium ions from alkyl halides in aprotic media, such as $SbF_5/SO_2FCl$. This acid system has been used to measure the position of the isopropyl ion plus cyclopentane equilibrium (See G. M. Kramer, *Int'l. Spectroscopy, J. Mass Spectroscopy*, 19, 139 (1976)), but interferring oxidation by the acid or trace protonic impurities makes it difficult to study equilbria involving tertiary cations and alkanes.

Unexpectedly, it has been found that oxidation is not a serious problem in aprotic non-reactive solutions of Lewis acid systems such as $AlBr_3/CH_2Cl_2$, $AlBr_3/CH_2Br_2$, $GaCl_3/CH_2Cl_2$, $GaCl_3/ClCH_2CH_2Cl$, $GaBr_3/CH_2Br_2$,

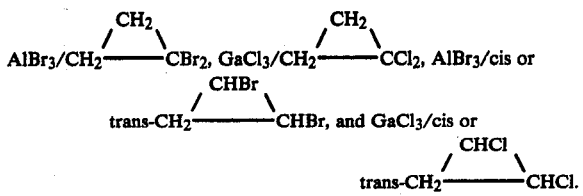

The stabilized, strong Lewis acid systems of the present invention have been found capable of stabilizing concentrated solutions of tertiary carbonium ions and they have been found useful in assessing hydride transfer equilibria between the t-butyl carbonium ion and isopentane, 2,3-dimethylbutane, 3,4-dimethylpentane, methylcyclopentane, adamantane and several other hydrocarbons.

These non-reactive aprotic Lewis acid solutions can be made while changing the ratio of the t-butyl halide to Lewis acid. It has been found that as the t-butyl halide-/Lewis acid ratio is increased from about 1/10 toward ½ with the $AlBr_3$ solutions or 1/1, with the $GaCl_3$, one principally increases the $R^+$ carbonium ion concentration. The solutions with ratios of t-butyl halide to Lewis acid of up to 1:2 have been found to be more stable with respect to side reactions. In $AlBr_3$ solutions the alkyl halide effectively titrates the acid ($AlBr_3$) and converts it into a stable salt, $R^{\oplus}Al_2X_7{}^{\ominus}$. Neither the salts nor excess $AlBr_3$ attack halogenated compounds such as $CH_2Cl_2$ at temperatures up to $-30°$ C., but the cation is active in all the processes needed for isomerization and alkylation. Specifically, these stabilized strong Lewis acid solutions (i.e., the strong Lewis acid dissolved in the non-reactive aprotic solvent) support extremely rapid intermolecular $H^{\ominus}$ transfer reactions with both tertiary and secondary hydride donors.

SUMMARY OF THE INVENTION

One aspect of the invention includes a catalyst precursor comprising a strong Lewis acid characterized as having a "Selectively Parameter" $(I/E)_{MCP}$ greater than about 0.5 dissolved in a non-reactive aprotic solvent for said strong Lewis acid, said aprotic solvent being selected from the group consisting of $C_1$-$C_3$ halogenated alkanes, halogenated cyclopropane and halogenated $C_2$-$C_3$ alkenes, wherein the $C_2$ and $C_3$ compounds have at least 2 halogen atoms, preferably Cl, Br or F.

The catalyst precursor of the present invention is preferably a liquid solution of the strong Lewis acid in the non-reactive aprotic solvent. The amount of the strong Lewis acid dissolved in the non-reactive aprotic solvent can range from a very dilute solution, e.g., greater than about 0.01 molar, of the strong Lewis acid, preferably a concentration ranging from greater than abut 0.1 molar. It will generally be convenient to employ the catalyst system of the invention in concentrations ranging from 0.5 to about 5 molar, preferably from about 0.5 to 3 molar, where the term "molar" herein refers to the number of moles per liter of strong Lewis acid in the solvent.

Another aspect of the present invention includes a catalyst composition which comprises an admixture of a strong Lewis acid characterized as having a "Selectivity Parameter" $(I/E)_{MCP}$ greater than about 0.5 dissolved in a non-reactive aprotic solvent, said aprotic solvent selected from the group consisting of halogenated $C_1$–$C_3$ alkanes, halogenated cyclopropane and halogenated $C_2$–$C_3$ alkenes (wherein the $C_2$ and $C_3$ compounds have at least 2 halogen atoms, preferably Cl, Br or F) and a conventional catalyst promoter. The term "conventional catalyst promoter" includes compounds such as hydrogen halides, e.g., HCl and HBr, t-butyl chloride, water, t-amyl alcohol and the like. If t-alkyl halides are used as promoters, they may be used in a mole ratio ranging from about 0.1 to 1, preferably from about 0.15 to 1 and more preferably ranging from about 0.2 to 0.5 moles per mole of the strong Lewis acid, e.g., $AlBr_3$, in the catalyst composition. Hydrogen halides such as HBr may be used as promoters in concentrations ranging from 0.1 to 10 weight percent of the solvent.

Another aspect of the invention includes a process for preparing the stable catalyst composition herein described, comprising: admixing a strong Lewis acid characterized as having a "Selectivity Parameter" $(I/E)_{MCP}$ greater than about 0.5 and a non-reactive aprotic solvent, said aprotic solvent selected from the group consisting of halogenated $C_1$–$C_3$ alkanes, halogenated cyclopropane and halogenated $C_2$–$C_3$ alkenes (wherein the $C_2$ and $C_3$ compounds have at least 2 halogen atoms) with a conventional catalyst promoter, e.g., an alkyl halide such as t-butyl halide at a temperature less than 0° C., preferably a temperature ranging from about −90° C. to about −50° C., and then warming the admixture, under agitating conditions until a clear homogeneous solution is formed.

The resulting solution is capable of containing large quantities of the alkyl cation and remains clear and stable at temperatures below 0° C. The process is particularly useful in preparing solutions of $AlBr_3$ dissolved in $CH_2Cl_2$ which undergoes rapid destructive halogen exchange reactions at ambient temperatures. The conventional catalyst promoters may be admixed with the strong Lewis acid/non-reactive aprotic solvent concurrently or sequentially after the strong Lewis acid has been dissolved in the non-reactive aprotic solvent.

Stil another aspect of the invention includes the use of the herein described catalyst composition to catalyze hydrocarbon conversion reactions, e.g., isomerization, selective olefin akylation, polymerization, "Paraffin alkylations", etc.

In one specific preferred embodiment of the invention, there is included the process of selectively alkylating propylene with isobutane in the presence of the herein described catalyst composition to obtain 2,2-dimethylpentane.

In another preferred embodiment, there is provided a process wherein butene-2 is alkylated in the presence of the herein described catalyst composition to obtain high yields of 2,2,3-trimethylpentane, a low concentration product produced by the traditional olefin alkylation using HF or $H_2SO_4$ as the acid catalyst.

DETAILED DESCRIPTION OF THE INVENTION

The strong Lewis acids to be used in accordance with the practice of the present invention, as indicated hereinabove, are characterized as having a "Selectivity Parameter" $(I/E)_{MCP}$ greater than about 0.5. Preferably, the strong Lewis acids will be comprised of the formula $MX_n$ wherein M is selected from the Group IIIA, elements of the Periodic Table, X is a halogen, preferably bromine or chlorine, n is the ratio of halogen atoms to atoms of M and varies from 1–8. The Periodic Table referred to is that described in "Encyclopedia of Chemistry", Reinhold Publishing Corporation, 2nd Ed. (1966) at page 790. The term "elements" as used herein refers to the metals and metalloids of the aforementioned Groups of the Periodic Table. The preferred Lewis acids are the bromides and chlorides of aluminum and gallium. Typical examples of the most preferred Lewis acids include: $AlBr_3$, $AlBr_2Cl$, $AlBrCl_2GaBr_3$, $GaBr_2Cl$, $GaBrCl_2$ and $GaCl_3$. The strong Lewis acid will, of course, be chosen such that it will dissolve in the nonreactive aprotic solvent. In this connection, $AlCl_3$ is generally not a desirable Lewis acid because it is poorly dissolved in most of the non-reactive aprotic solvents of the invention.

The "Selectivity Parameter" $(I/E)_{MCP}$ is the ratio of the rate of isomerization of an equilibrated and tritiated mixture of 2-methylpentane, 3-methylpentane and 2,3-dimethylbutane to 2,2-dimethylbutane and n-hexane divided by the rate of exchange of the tritium atoms with protons on methylcyclopentane. In $H_2SO_4$ or HF there is very little isomerization and much exchange so that $(I/E)_{MCP}$ is ~0, while in 2M $AlBr_3$/HBr the value is >5.

The "non-reactive" aprotic solvents to be used in the practice of the present invention are those solvents which neither yield a proton to the solute, nor gain one from it (they are neither an acid nor base). The term "nonreactive" is meant to include compounds which do not undergo an elimination reaction, or an isomerization or reduce the acidity of the Lewis acid by acting as a Lewis base. For example, isopropyl chloride reacts with $AlBr_3$, and, therefore, is not desirable as a "non-reactive" aprotic solvent to be considered for use in the practice of the present invention.

Generally speaking the non-reactive aprotic solvents of the present invention will include the halogenated $C_1$–$C_3$ alkanes, halogenated cyclopropane or halogenated $C_2$–$C_3$ alkenes (wherein the $C_2$–$C_3$ compounds contain 2 or more halogen atoms per mole and the halogens are preferably chlorine, bromine or fluorine). Non-limiting examples of suitable non-reactive aprotic solvents include the following compounds: methylene chloride, methylene bromide, 1,2-dichloroethane, 1,1-dibromocyclopropane, 1,1-dibromocyclopropane, cis or trans-1,2-dichlorocyclopropane, and cis or trans-1,2-dibromocyclopropane.

The catalyst precursor system is prepared by simply dissolving the Lewis acid is a purified non-reactive solvent under agitating conditions. The mixing is preferably conducted at relatively low temperatures and then the system is gradually warmed until a clear solution is obtained. This procedure is particularly important in the case of the $AlBr_3/CH_2Cl_2$ system because at ambient temperature conditions it undergoes an exothermic halide exchange which can lead to dangerous overheating or an explosion. The exchange ultimately forms AlCl$_3$ which precipitates and renders the systems less useful as a catalyst. This problem can be avoided by warming a mixture of AlBr$_3$/CH$_2$Cl$_2$ prepared at $-80°$ C., until the AlBr$_3$ dissolves and then cooling the solutions to about $-40°$ C. In this manner clear 1M solutions are obtained which proton nmr spectroscopy indicates to contain only traces of CH$_2$BrCl.

In preparing the strong acid catalyst precursors and catalyst systems of the invention it is necesary to keep the solutions away from atmospheric moisture. Therefore, it is desirable to carry out the reactions in preparing the catalyst systems and the reactions with the same under a nitrogen atmosphere.

The catalyst system of the present invention can be put to use in a plurality of hydrocarbon conversion processes by simply contacting a hydrocarbon feed with the aforedescribed catalyst system at conditions of temperatures and pressures wherein the catalyst is liquid. The catalyst system is suited for carrying out isomerizations, olefin alkylations, polymerizations and "Paraffin alkylations" of hydrocarbon feedstocks.

Paraffinic hydrocarbon feedstocks that are suitable for use in the present invention include the aliphatic and cycloaliphatic hydrocarbons. The aliphatic hydrocarbons (straight and branched chain materials) contain 4 to 12 carbon atoms per molecule (C$_4$–C$_{12}$), preferably 4 to 8 carbon atoms (C$_4$–C$_8$), and may be exemplified by butane, pentane, hexane, heptanes, their isomers and the like. The cycloaliphatic hydrocarbons (naphthenes) contain 6 to 15 carbon atoms per molecule, preferably 6 to 12 carbon atoms, and may be exemplified by methylcyclopentane, dimethylcyclopentane, ethylcyclohexane, n-pentylcyclohexane and the like.

It should be understood that use of paraffinic hydrocarbon feedstocks having more than 12 carbon atoms per molecule, e.g.; polymers, paraffinic waxes and the like, are contemplated in the present invention. However, such feedstocks will not be alkylated (in the case of the "Paraffinic alkylation" process of the invention) because paraffinic species having more than about 8 carbon atoms per molecule are less stable in a strong acid environment and will tend to break down to more stable, i.e., lower carbon number, reaction intermediates in the acid solution. The lower carbon number intermediates will then be alkylated according to the present invention to form desired liquid products. It is believed that cycloaliphatic hydrocarbons will behave in a similar manner but at a slower reaction rate.

The catalyst system of the present invention is suitable for alkylating or isomerizing the paraffinic feedstocks hereinabove described. For example, "Paraffin alkylation" may be carried out by alkylating a paraffin with another paraffin. For example, a paraffinic feedstock containing smaller paraffins, i.e., isobutane, isopentanes, isohexanes or mixtures thereof, can undergo alkylation with larger paraffins, i.e., paraffins or a mixture of paraffins having more than 6 carbon atoms, to form intermediate molecular weight materials. Thus, isobutane can undergo a "Paraffin alkylation" reaction with heptane to form pentanes and hexanes. Of course, these paraffinic feedstocks may be isomerized by contacting the feeds with the catalyst system of the invention under isomerization conditions (i.e., lower temperatures) or under H$_2$ pressure until an isomerized product is obtained.

The preferred alkylation process of the invention will involve the alkylation of a paraffinic hydrocarbon, preferably an isoparaffinic hydrocarbon with an olefin (i.e., olefin alkylation). Olefins containing 2 to 8 carbon atoms per molecule are suitable for use in the olefin alkylation process of the invention while olefins containing 2 to 6 carbon atoms per molecule are particularly preferred. The reaction mixture may also contain some amounts of diolefins. Although it is desirable from an economic viewpoint to use the normally gaseous olefins as reactants, normally liquid olefins may be used. The present invention also contemplates the use of polymers, copolymers, interpolymers, crosspolymers, etc. of the above-mentioned olefins, as for example, the diisobutylene and triisobutylene polymers, the codimer of normal butylenes and the like. These materials are broken down into smaller units which can then be alkylated according to the process of the present invention. The use of mixtures of two or more of the above-described olefins is envisioned for use in the process of the present invention.

The present catalyst systems are particularly suited for use in refinery "Paraffin" or olefin alkylation and isomerization processes. The process of this invention contemplates the use of various refinery streams as feedstocks. Thus, C$_2$, C$_3$, C$_4$ and/or C$_5$ olefin cuts from thermal and/or catalytic cracking units; field butanes which have been subjected to prior isomerization and partial dehydrogenation treatment; refinery stabilizer bottoms; normally gaseous products from sulfuric acid or phosphoric acid catalyzed polymerization and copolymerization processes; and products, normally gaseous in character from thermal and/or catalytic cracking units, are all excellent feedstocks for the present process. Such feeds are preferably dried to control excess water buildup, i.e., about 0.5 to 15 wppm, preferably about 0.5 to 2 wppm of water before entering the reactor.

The process catalyst system is somewhat sensitive to impurities such as water. Therefore, the present alkylation, isomerization and polymerization processes should be conducted in the absence of large amounts of moisture, and preferably under substantially anhydrous conditions.

Preferably, the processes of the present invention will be carried out in the substantial absence of aromatic compounds. In the processes such as alkylation, the aromatic compounds will be readily alkylated to more basic compounds which, in turn, will dilute the acid catalyst and hence the effectiveness of the catalyst. Thus, although aromatic compounds may be present in the feedstock, it is preferred that the processes of the present invention be conducted in their substantial absence.

In case of the olefin alkylation process of the invention, the molar ratio of olefin to paraffin in the feed may range from 1:1 to 1:200, preferably from 1:3 to 1:50. In general, a high dilution of the olefin is preferred in order to prevent competitive side reactions such as olefin polymerization and self-alkylation reactions. In addition, the concentration of olefins dispersed in the acid should be low to allow substantially all of the olefin to be alkylated. Thus, preferred operations are at low olefin feed rates relative to catalyst inventory; i.e., at low olefin space velocity. In the case of "Paraffin alkylation", an excess of the smaller paraffin relative to the larger paraffin, should be maintained. Typically, the molar ratio of smaller paraffin to larger paraffin in the reaction zone should be in the range of from about 2:1 to about 100:1, preferably from about 3:1 to about 20:1.

It is preferred that the processes of the invention, especially the isomerization and olefin alkylation processes be conducted in the presence of at least one cracking inhibitor, e.g., hydrogen. Inhibitors such as hydrogen serve as moderators for cracking reactions that might occur and will hydrogenate free intermediates, polymeric materials as well as other unsaturated materials, which might be formed during the reaction and thus, be present in the acid phase. This also has the effect of increasing the life of the catalyst system.

The amount of hydrogen present in the acid catalyst system during isomerization of olefin alkylation is not critical, provided there is an amount sufficient to saturate isomerization and/or alkylation sludge precursors, i.e., to saturate the intermediate products formed during the break-up of any polymers formed during isomerization or alkylation. Amounts ranging from about 0.1 to about 5 wt. % based on hydrocarbon feed are sufficient although greater amounts may be used. The hydrogen may be present in the form of a hydrogen-containing gas which may be obtained from any number of sources including commercially available pure hydrogen, naphtha reformers, hydrogen plants, as well as the off-gases from any hydrotreating process or hydrogen donor organic molecules such as tetralin, methylcyclohexane, decalin, isobutane and the like. The term "hydrotreating process" is meant to include hydrofining, hydrocracking, hydrosulfurization and the like or synthetic schemes in which hydrogen is a product. The hydrogen-containing gas may be pure or contain other gaseous materials such as light hydrocarbons ($C_1$–$C_8$), carbon monoxide, carbon dioxide, hydrogen sulfide and the like. The hydrogen-containing gas may be introduced into the isomerization or alkylation process alone or be mixed with the hydrocarbon feed prior to said introduction. Preferably the hydrogen-containing gas will be dry.

In the processes of the present invention (alkylation, isomerization and polymerization), the reactants are contacted in the presence of a catalyst for a time sufficient to effect the degree of conversion desired. In general, the contact time is subject to wide variation. The length of the contact time depends in part upon the temperature, the reactants used and the catalyst concentration employed. Typical contact times will range from about 0.05 seconds to several hours, preferably from about 0.05 seconds to about 1 hour, more preferably from about 0.05 seconds to about 45 minutes.

The amount of catalyst employed for carrying out the processes of the present invention can vary appreciably. In general, in the case of the olefin alkylation process, the volumetric space velocity, based on the olefin will range from about 0.01 to about 1 V/Hr/V, preferably from about 0.04 to about 0.2 V/Hr/V (volume of olefin per hour per volume of catalyst). For isomerization and paraffin alkylation space velocities of 0.05 to 5 volumes of hydrocarbon per hour per volume of the acid catalyst solution will be used. In polymerization reactions of olefins the olefin space velocity may be as high as 10,000 V/V/Hr.

In general, the processes of the present invention will be carried out at temperatures ranging from about −100° C. to about 50° C., preferably from about −30° C. to 20° C. The lower temperatures are preferred for polymerization and olefin alkylation, the higher temperatures are preferred for paraffin alkylation and isomerization.

The carbonium ion concentration used will generally be lower for polymerization than for the other processes. For polymerization, concentrations of $10^{-4}$ to $10^{-2}$ molar are usually used while for the olefin alkylation, "Paraffin Alkylation" and isomerization reactions concentrations of 0.5 to 2.5 molar are preferred.

The preferred polymerization feedstock will be propylene or isobutylene and their respective mixtures with 1,3-butadiene and/or cyclopentadiene.

The pressure at which the processes of the invention is carried out will depend upon the feedstream being processed, the reaction diluent, the hydrogen purity (i.e., less hydrogen present will require increased pressure) as well as other process variables. In general, the pressure should be sufficient to maintain at least a portion of one of the catalyst components in the liquid phase. Preferably the isomerization processes of the invention will be conducted in the presence of hydrogen whose partial pressure should be at least 0.1 atmospheres and may range from about 0.1 to about 100 atmospheres, preferably from about 0.1 to about 50 atmospheres and most preferably from about 0.3 to about 25 atmospheres. The total pressure may range from about 0.1 to about 150 atmospheres. The processes of the present invention may be conducted in the presence of an inert atmosphere such as nitrogen. It is preferred that the processes be conducted in the substantial absence of an oxygen-containing gas, i.e., less than about 1 wt. % oxygen based on the inert atmosphere.

The alkylation, isomerization or polymerization processes of the present invention may be conducted in a batch, intermittent or continuous operation. Preferably, the invention is carried out in a continuous manner to minimize further reaction of the product or products formed. It has been generally established that in alkylation processes, the more intimate the contact between the feedstock and the catalyst the better the yield of saturated product obtained. Thus, the apparatus employed may be of a conventional nature and comprise a single reactor or multiple reactors equipped with efficient stirring devices such as mechanical agitators, turbomixers, jet mixers and the like. One or more reactants may be introduced into the reaction zone through dispersion devices such as jets of restricted internal diameter, porous thimbles, and the like. The hydrocarbon paraffin-olefin or paraffin-paraffin phase, the catalyst phase and the hydrogen containing gas may be passed through one or more reactors in concurrent, cross-current, or countercurrent flow. After a sufficient period of time, unreacted reactants, partially deactivated catalyst, inhibitors and heavier products of the reaction may be separated from the desired alkylation product and from one another, such as by distillation, and returned in whole or in part to the alkylation zone. If desired, a portion of the partially deactivated catalyst can be regenerated or reactivated by any suitable treatment and returned to the alkylation process.

As in other alkylation processes, more accurate control of the quality of the final product may be obtained if the reaction system is provided with a recycling feature wherein the partially converted hydrocarbons are mixed with fresh feed and returned to the feed dispersion device in the reaction zone. However, due to the high conversion efficiency of the present catalyst system, it is preferred to effect alkylation in a once-through operation with short contact times.

Reactions involving the use of the present catalyst systems can be conducted in vessels fabricated from carbon steels provided that excessive temperatures are not to be used and provided that the reaction system is maintained in a substantially anhydrous condition. Teflon, Carpenter 20 Cb-3 (Alloy 20) steel or Monel may also be used in the fabrication of reaction equipment.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944; 2,479,366; 2,701,184; 2,717,913; 2,775,636; U.K. Pat. Nos. 543,046; 577,869; 731,806; 738,348; 803,458; 804,966 and 881,892, the disclosures of which are incorporated herein by reference.

The present invention may be better understood by reference to the following examples which are presented for illustrative purposes only and are not intended to unduly restrict the limits of the claims appended hereto.

EXAMPLE 1

Catalyst Preparation: $GaCl_3$ Dissolved in $CH_2Cl_2$

One ml of a 2 M solution of $GaCl_3$ (freshly sublimed) in $CHCL_2$ is placed in a glass flask containing a magnetic stirrer at ambient temperature. The flask is flushed with nitrogen and cooled to $-50°$ C. and stirred. To this solution there is then slowly added one ml of a 0.4 M solution of t-butyl chloride in $CH_2Cl_2$. This yields 2 ml of 0.2 M solution of t-butyl cations in a 1 M solution of $GaCl_3$ (as determined by proton nmr spectroscopy). The solution may now be used to catalyze isomerization, alkylation or polymerization in the manner described hereinabove.

Alkylation Reaction: Alkylation of Isobutane with Propylene

The alkylation of isobutane with propylene is carried out in the following manner. A 0.8 M t-butyl chloride solution in $CH_2Cl_2$ is prepared by adding 0.1760 ml t-butyl chloride to enough $CH_2Cl_2$ to provide 2 ml of solution. This solution is added at $-50°$ C. to a solution of 1.0 ml of 2.0 M $GaCl_3$ in $CH_2Cl_2$ mixed with 0.6 ml of isobutane to obtain the alkylation catalyst system.

To this flask containing the catalyst system described above there is added 0.7 ml of a 10:1 mixture of isobutane and propylene at $-78°$ C. and then an additional $8 \times 10^{-4}$ moles of gaseous propylene are added to the catalyst system. (These components are distilled into the flask). The reactor now contains $17 \times 10^{-4}$ moles of propylene, $17 \times 10^{-3}$ moles of isobutane, and $1.6 \times 10^{-3}$ moles of t-butyl cations.

The solution is stirred for several minutes at $-78°$ C. and upon settling separates into 2 phases. The upper hydrocarbon phase is removed by vacuum distillation while warming slowly to room temperature. The solution is analyzed by gas chromatography and found to contain 2,2-dimethylpentane and 3,3-dimethylpentane as the only $C_7$ paraffins. The yield of the $C_7$ reaction products based on propylene feed is estimated at about 10 percent.

EXAMPLE 2

Catalyst Preparation: $AlBr_3$ Dissolved in $CH_2Br_2$

2 M solutions of $AlBr_3$ in $CH_2Br_2$ are prepared by mixing freshly sublimed $AlBr_3$ and distilled $CH_2Br_2$ at ambient temperatures in a nitrogen environment. One ml of this solution is placed in a glass flask, cooled to $-30°$ C. and stirred magnetically. To this solution there is slowly added 1 ml of a 0.4 ml solution of t-butyl bromide in $CH_2Br_2$. The solution nearly instantly forms a 0.2 M solution of $t\text{-}C_4H_9^+Al_2Br_7^-$ which is detected by proton nmr spectroscopy.

The catalyst thus prepared is useful in alkylating isoparaffinic feedstocks with olefins, isomerizing $C_4$–$C_7$ normal paraffin and/or $C_6$–$C_{10}$ naphthene, etc. and polymerizing olefins in the manner described hereinabove.

GENERAL DISCUSSION

The alkylation of isobutane with propylene at $-50°$ C. in $GaCl_3/CH_2Cl_2$ gave a small yield of a $C_7$ product which appears to be a mixture of only 2,2-dimethylpentane and 3,3-dimethylpentane. The alkylate yield crudely corresponds to 10 percent of the olefin. The other 90 percent resulted in undetected products which may be unionized alkyl chlorides left on $GaCl_3$ after separation. Both $C_7$ products are tentatively identified on the basis of GC retention times. The 2,2-dimethylpentane being deduced by "spiking" the product with a known sample of 2,2-dimethylpentane and finding a single GC component. The analysis was run under conditions in which 2,2-dimethylpentane could be separated from 2,4-dimethylpentane and 2,2,3-trimethylbutane, the nearest other $C_7$ compounds, if they were present.

In the alkylation example (above) there were some unidentified heavy compounds which may be $C_7$ alkyl chlorides, but extremely few low molecular weight cracking components like isopentane or isohexanes. The analysis of the light components is somewhat in error since the $i\text{-}C_4H_{10}$ analysis was much less than it could have been, meaning that isobutane was lost in the analytical or sample collecting procedure. Nevertheless, the selective production of 2,2-dimethylpentane and 3,3-dimethylpentane constitutes the first solid evidence that the secondary ions are trappable intermediates in propylene alkylation.

The formation of 3,3-dimethylpentane is quite unexpected. The formation of 3,3-dimethylpentane might be reasonable if the 2,3-dimethylpentane ion is not easily trapped by hydride transfer from isobutane because of either steric constraints or the "windshield wiping" action of the tertiary hydride which should be undergoing very fast 1,2-shifts. Then, as the ion slowly isomerizes to the 3,3-dimethylpentane structure, the latter might be successfully trapped.

Alkylation with $GaCl_3/CH_2Cl_2$ at $-30°$ C. gave a relatively small yield of alkylate that is mainly 2,2-dimethylpentane and 3,3-dimethylpentane with some 2,4-dimethylpentane. This sample also contained relatively large amounts of isopentane and $C_6$ isomers, indicative of the relatively poor alkylation conditions used.

Based on preliminary experiments attempted olefin alkylations using the $AlBr_3/CH_2Br_2$ system at $-30°$ C. yielded alkylate product, but the yields were relatively low. The $C_8$ products appear to contain a relatively large amount of iso-pentane, but the hydrocarbon recovery was too small to resolve by G. C. analysis. The major component of the sample was the aprotic solvent, $CH_2Br_2$. The $AlBr_3/CH_2Br_2$ solutions appeared to be more nucleophilic and less ion stabilizing than $AlBr_3/CH_2Cl_2$. Both t-butyl bromide and chloride behaved similarly until the 1:2 ratio was reached and both yielded a shifted butyl signal at slightly higher ratios.

It was also found that both methylene chloride and 1,2-dichloroethane form solutions with GaCl₃ that stabilize the t-butyl ion. The ion is again formed with the least formation of side products at R-Cl/GaCl₃ ratios below 1:2. At ratios between this and 1:1 in methylene chloride one finds a slight upfield shift of the t-butyl signal and the formation of small signals that appear as sharp singlets at +145.5, +187.5 and +232.5 cps. The 1,2-dichloroethane solvent was also effective at stabilizing t-butyl ions at similar conditions as CH₂Cl₂. Both of the GaCl₃ systems (i.e., GaCl₃/CH₂Cl₂ and GaCl₃/ClCH₂CH₂Cl systems) tested appeared to yield both monomeric and dimeric anions with the t-butyl cation.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A stable acid system comprising a Lewis acid being characterized as having a "Selectivity Parameter" $(I/E)_{MCP}$ greater than about 0.5 and being represented by the formula MXn wherein M, is a Group IIIA element of the Periodic Table, X is a halogen and n is the ratio of halogen atoms to atoms of M dissolved in a non-reactive aprotic solvent selected from the group consisting of methylene chloride, methylene bromide, 1,2-dichloroethane, 1,1-dibromocyclopropane, 1,1-dichlorocyclopropane, cis or trans-1,2-dichlorocyclopropane and cis or trans-1,2-dibromocycloproane, and wherein the concentration of said Lewis acid in the non-reactive aprotic solvent is greater than about 0.01 molar.

2. The stable acid system of claim 1 wherein the Lewis acid is selected from the group consisting of AlBr₃, AlBr₂Cl, AlBrCl₂, GaBr₃, GaBrCl₂ and GaCl₃.

3. The stable acid system of claim 1 wherein the Lewis acid is selected from the group consisting of AlBr₃, GaBr₃ and GaCl₃.

4. The acid system of claim 1 wherein the concentration of the Lewis acid in the non-reactive aprotic solvent ranges from 0.1 to about 5 molar.

5. The acid system of claim 4 wherein the mole ratio of the Lewis acid to the non-reactive aprotic solvent ranges from about 0.5 to about 3 molar.

6. The stable acid system of claim 1 wherein the Lewis acid is selected from the group consisting of AlBr₃, GaBr₃ and GaCl₃ and the non-reactive aprotic solvent is selected from the group consisting of methylene chloride and methylene bromide, and the concentration of the Lewis acid in the non-reactive aprotic solvent ranges from about 0.1 to about 5 molar.

7. A stable catalyst composition which comprises an admixture of (a) a Lewis acid characterized as having a "Selectivity Parameter" $(I/E)_{MCP}$ greater than about 0.5 and being represented by the formula MXn wherein M is a Group IIIA element of the Periodic Table, X is a halogen and n is the ratio of halogen atoms to atoms of M, (b) a nonreactive aprotic solvent selected from the group consisting of methylene chloride, methylene bromide, 1,2-dichloroethane, 1,1-dichlorocyclopropane, 1,1-dibromocyclopropane, cis or trans-1,2-dichlorocyclopropane and cis or trans-1,2-dibromocyclopropane, and wherein the concentration of said Lewis acid in the non-reactive aprotic solvent is greater than 0.01 molar and (c) an effective amount of a catalyst promoter; selected from the group consisting of water, hydrogen halides, t-amyl alcohol and t-alkyl halides 8. The catalyst composition of claim 7 wherein the Lewis acid is selected from the group consisting of AlBr₃, AlBr₂Cl, AlBrCl₂, GaBr₃, GaBr₂Cl, CaBrCl₂ and GaCl₃.

9. The catalyst composition of claim 7 wherein the non-reactive aprotic solvent is selected from the group consisting of methylene chloride and methylene bromide.

10. The catalyst composition of claim 7 wherein the catalyst promoter is selected from the group consisting of t-butyl chloride and t-butyl bromide.

11. The catalyst composition of claim 7 wherein the concentration of the Lewis acid in the non-reactive aprotic solvent ranges from about 0.1 to about 5 molar.

12. A stable catalyst composition comprising an admixture of a Lewis acid selected from the group consisting of AlBr₃, GaBr₃ and GaCl₃, a non-reactive aprotic solvent selected from the group consisting of methylene bromide and methylene chloride and a promoter selected from the group consisting of t-butyl bromide and t-butyl chloride, wherein the concentration of the Lewis acid in the non-reactive aprotic solvent ranges from about 0.5 to about 3 molar.

13. A stable catalyst composition comprising an admixture of (a) a Lewis acid being characterized as having a "Selectivity Parameter" $(I/E)_{MCP}$ greater than about 0.5 and being represented by the formula MXn, wherein M is a Group IIIA element of the Periodic Table, X is a halogen and n is the ratio of halogen atoms to atoms of M dissolved in (b) a non-reactive aprotic solvent selected from the group consisting of halogenated $C_1$–$C_3$ alkanes, halogenated cyclopropane and halogenated $C_2$–$C_3$ alkenes, wherein the $C_2$–$C_3$ compounds contain at least 2 halogen atoms per mole of compound, and wherein the concentration of the Lewis acid in the non-reactive aprotic solvent is greater than 0.01 molar, and (c) an effective amount of a promoter selected from the group consisting of t-butyl bromide and t-butyl chloride.

14. The stable catalyst composition of claim 13 wherein the Lewis acid is selected from the group consisting of AlBr₃, AlBr₂Cl, AlBrCl₂, GaBr₃, GaBr₂Cl, GaBrCl₂ and GaCl₃.

15. The stable catalyst composition of claim 14 wherein the Lewis acid is selected from the group consisting of AlBr₃, GaBr₃ and GaCl₃.

16. The stable catalyst composition of claim 13 wherein the non-reactive aprotic solvent is selected from the group consisting of methylene chloride, methylene bromide, 1,2-dichloroethane, 1,1-dibromocyclopropane, 1,1-dichlorocyclopropane, cis or trans-1,2-dichlorocyclopropane and cis or trans-1,2-dibromocyclopropane.

17. The stable catalyst composition of claim 13 wherein the concentration of the Lewis acid in the non-reactive aprotic solvent ranges from 0.1 to about 5 molar.

18. The stable catalyst composition of claim 17 wherein the molar ratio of the Lewis acid to the nonreactive aprotic solvent ranges from about 0.5 to about 3 molar.

19. The stable catalyst composition of claim 13 wherein the Lewis acid is selected from the group consisting of $AlBr_3$, $GaBr_3$ and $GaCl_3$ and the non-reactive aprotic solvent is selected from the group consisting of methylene chloride and methylene bromide, the concentration of the Lewis acid in the non-reactive aprotic solvent ranges from about 0.1 to about 5 molar and the mole ratio of the Lewis acid to the non-reactive aprotic solvent ranges from about 0.5 to about 3 molar.